United States Patent
Kengla (10) Patent No.: US 11,046,823 B2
(45) Date of Patent: Jun. 29, 2021

(54) COMPOSITION WITH POLYMER AND CERAMIC AND METHODS OF USE THEREOF

(71) Applicant: WAKE FOREST UNIVERSITY HEALTH SCIENCES, Winston-Salem, NC (US)

(72) Inventor: Carlos Kengla, Winston-Salem, NC (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 76 days.

(21) Appl. No.: 16/322,219

(22) PCT Filed: Aug. 2, 2017

(86) PCT No.: PCT/US2017/045065
§ 371 (c)(1),
(2) Date: Jan. 31, 2019

(87) PCT Pub. No.: WO2018/026902
PCT Pub. Date: Feb. 8, 2018

(65) Prior Publication Data
US 2019/0194401 A1   Jun. 27, 2019

Related U.S. Application Data

(60) Provisional application No. 62/370,526, filed on Aug. 3, 2016, provisional application No. 62/529,661, filed on Jul. 7, 2017.

(51) Int. Cl.
C08J 3/205 (2006.01)
A61L 27/46 (2006.01)
(Continued)

(52) U.S. Cl.
CPC ............... *C08J 3/205* (2013.01); *A61L 27/46* (2013.01); *A61L 27/56* (2013.01); *A61P 19/08* (2018.01);
(Continued)

(58) Field of Classification Search
CPC ...................................................... A61L 27/46
See application file for complete search history.

(56) References Cited

U.S. PATENT DOCUMENTS 5,281,265 A   1/1994 Liu
5,757,649 A   5/1998 Kato
(Continued)

FOREIGN PATENT DOCUMENTS

WO   2013/023064   2/2013
WO   2014/168585   10/2014

OTHER PUBLICATIONS

Metwally, H.A., Ardazishvili, R.V., Severyukhina, A.N. et al. The Influence of Hydroxyapatite and Calcium Carbonate Microparticles on the Mechanical Properties of Nonwoven Composite Materials Based on Polycaprolactone. BioNanoSci. 5, 22-30 (2015) (Year: 2015).*

(Continued)

*Primary Examiner* — Michael F Pepitone
(74) *Attorney, Agent, or Firm* — Myers Bigel, P.A (57) ABSTRACT

Provided herein are improved compositions and methods of making and using the same, the composition comprising a polymer and a ceramic present at a ratio of from 3:1 to 1:3 of polymer:ceramic by weight, wherein the composition comprises or is a composite of the polymer and the ceramic having improved printability and/or having an improved elastic modulus and/or improved stress at failure (e.g., as compared to a blend of the polymer and the ceramic).

10 Claims, 9 Drawing Sheets

(51) Int. Cl.
  *C09D 11/10* (2014.01)
  *A61P 19/08* (2006.01)
  *A61L 27/56* (2006.01)
  *B29C 64/118* (2017.01)
  *B29C 64/209* (2017.01)
  *C08J 3/12* (2006.01)
  *C08K 3/32* (2006.01)
  *B33Y 10/00* (2015.01)
  *B33Y 70/00* (2020.01)
  *B33Y 80/00* (2015.01)
  *B29L 31/00* (2006.01)
  *C08J 9/00* (2006.01)

(52) U.S. Cl.
  CPC .......... *B29C 64/118* (2017.08); *B29C 64/209* (2017.08); *C08J 3/12* (2013.01); *C08K 3/32* (2013.01); *C09D 11/10* (2013.01); *A61L 2430/02* (2013.01); *B29L 2031/7532* (2013.01); *B33Y 10/00* (2014.12); *B33Y 70/00* (2014.12); *B33Y 80/00* (2014.12); *C08J 9/008* (2013.01); *C08J 2367/04* (2013.01); *C08K 2003/325* (2013.01); *C08K 2201/005* (2013.01)

(56) References Cited

U.S. PATENT DOCUMENTS

| | | | |
|---|---|---|---|
| 5,930,152 | A | 7/1999 | Dumont et al. |
| 6,379,593 | B1 | 4/2002 | Datzmann et al. |
| 6,594,539 | B1 | 7/2003 | Geng |
| 6,696,073 | B2 | 2/2004 | Boyce et al. |
| 6,730,252 | B1 | 5/2004 | Teoh et al. |
| 6,773,713 | B2 | 8/2004 | Bonassar et al. |
| 6,775,581 | B2 | 8/2004 | Landers et al. |
| 6,804,568 | B1 | 10/2004 | Miyazaki et al. |
| 6,869,445 | B1 | 3/2005 | Johnson |
| 7,308,386 | B2 | 12/2007 | Landers et al. |
| 7,413,597 | B2 | 8/2008 | Lewis |
| 7,472,044 | B2 | 12/2008 | Landers et al. |
| 7,968,026 | B1 | 6/2011 | Teoh et al. |
| 8,071,007 | B1 | 12/2011 | Teoh et al. |
| 8,702,808 | B2 | 4/2014 | Teoh et al. |
| 2007/0009606 | A1* | 1/2007 | Serdy ............... A61L 27/56 424/497 |
| 2007/0299156 | A1 | 12/2007 | Brown |
| 2011/0300626 | A1* | 12/2011 | Arinzeh ............. D01D 5/0007 435/366 |
| 2012/0089238 | A1 | 4/2012 | Kang et al. |
| 2014/0358238 | A1 | 12/2014 | Teoh et al. |
| 2015/0037385 | A1 | 2/2015 | Shah et al. |
| 2015/0119994 | A1 | 4/2015 | Kang et al. |

OTHER PUBLICATIONS

Written Opinion and International Search Report corresponding to International Patent Application No. PCT/US2017/045065, dated Oct. 13, 2017, 8 pages.

Metwally et al. "The Influence of Hydroxyapatite and Calcium Carbonate Microparticles on the Mechanical Properties of Nonwoven Composite Materials Based on Polycaprolactone" BioNanoScience, 5(1):22-30 (2014).

Kengla, Carlos V., "Towards Personalized Bone Tissue Engineering: Clinically Inspired Application of 3D Bioprinting" Ph.D. Dissertation, Wake Forest University Graduate School of Arts and Sciences, Aug. 2017, published Feb. 21, 2018.

Goh et al., The use of a polycaprolactone-tricalcium phosphate scaffold for bone regeneration of tooth socket facial wall defects and simultaneous immediate dental implant placement in Macaca fascicularis, Journal of Biomedical Materials Research A, May 2014, vol. 102A, Issue 5, pp. 1379-1388.

Hutmacher et al., Mechanical properties and cell cultural response of polycaprolactone scaffolds designed and fabricated via fused deposition modeling, Journal of Biomedical Materials Research, vol. 55, Issue 2, 2001, pp. 203-216, abstract.

Liu et al., Review: Development of clinically relevant scaffolds for vascularized bone tissue engineering, Biotechnology Advances, vol. 31, 2013, pp. 688-705.

Lohfeld et al., Fabrication mechanical and in vivo performance of polycaprolactone/tricalcium phosphate composite scaffolds, Acta Biomaterialia, vol. 8, Issue 9, 2012, pp. 3446-3456.

Schumann et al., Design of Bioactive Multiphasic PCL/Collagen Type I and Type II-PCL-TCP/Collagen Composite Scaffolds for Functional Tissue Engineering of Osteochondral Repair Tissue by Using Electrospinning and FDM Techniques, Chapter 6: Biomaterials/Scaffolds, in Methods in Molecular Medicine, 2nd ed,: Tissue Engineering (H. Hauser and M. Russenegger, eds., Humana Press Inc., Totowa, NJ), pp. 101-124.

Yeo et al., Surface modification of PCL-TCP scaffolds in rabbit calvaria defects: Evaluation of scaffold degradation profile, biomechanical properties and bone healing patterns, Journal of Biomedical Materials Research Part A, vol. 93A, Issue 4, 2010, pp. 1358-1367.

Kang et al., A 3D bioprinting system to produce human-scale tissue constructs with structural integrity, Nature Biotechnology, vol. 34, 2016, pp. 312-319, with Online Methods (3 pages).

\* cited by examiner

COMPOSITION WITH POLYMER AND CERAMIC AND METHODS OF USE THEREOF

RELATED APPLICATIONS

This application claims the benefit of U.S. Provisional Patent Application Ser. No. 62/370,526, filed Aug. 3, 2016, and U.S. Provisional Patent Application Ser. No. 62/529,661, filed Jul. 7, 2017, the disclosures of each of which are incorporated herein by reference in their entirety.

STATEMENT OF GOVERNMENT SUPPORT

This invention was made with Government support under grant number W81XWH-14-2-0004 awarded by the Armed Forces Institute for Regenerative Medicine. The Government has certain rights to this invention.

BACKGROUND

Tricalcium phosphate (TCP) has been demonstrated in the literature to be similar to hydroxyapatite found in bone, and similarly promotes bone integration and regeneration. However, TCP is difficult to work with as an implant material. As a ceramic, it undergoes brittle fracture when loaded to failure. Implants fashioned from TCP also demonstrate an inability to withstand loading in bony defects.

Utilizing TCP particles as a part of a composite material has shown better performance. A polymer, such as polycaprolactone (PCL), can stabilize the composite under shear stress while TCP provides chemical and thermodynamic properties favorable for bone regeneration. PCL is a biodegradable polyester that has been utilized in medicine for many years, with applications in suture material, orthopedic implants, and degradable mesh devices.

However, to date, successful incorporation of TCP into PCL to form a useable material has been limited to 20% by weight. For example, Goh et al., J. Biomed. Materials Res. A, May 2014, vol. 102A, issue 5, reported the use of a PCL-TCP scaffold for bone regeneration and immediate dental implant comprised of 20% TCP by weight. However, it was reported that much of the scaffold was still present in vivo at 6 months, though a scaffold that degrades in about 5-6 months is considered ideal for bone regeneration and remodeling. In addition, minimal bone ingrowth was noted. See also Schumann et al., Chapter 6: Biomaterials/Scaffolds, in Methods in Molecular Medicine, 2nd ed.: Tissue Engineering (H. Hauser and M. Russenegger, eds., Humana Press Inc., Totowa, N.J.), which also describes use of a PCL-TCP mixture having 20% by weight TCP.

Although there have been reports in which a mixture of up to 50% by weight TCP blended with PCL was used in selective laser sintering (SLS) fabrication of scaffolds, it could not be used for experiments due to mechanical instability. See Lohfeld et al., Acta Biomaterialia, 8:3446-3456, 2012.

The use of a biodegradable polymer/ceramic composite during biofabrication also remains a challenge due to the interfacing of the material with the deposition/fabrication hardware because the materials must be sufficiently extrudable in order to be deposited.

Accordingly, there is a need for improved polymer ceramic compositions, especially those useful in biofabrication.

SUMMARY

Provided herein is an improved composition comprising a polymer (e.g., a biocompatible polymer such as PCL), and a ceramic (e.g., a biocompatible ceramic such as TCP), the polymer and the ceramic present in the composition at a ratio of from 3:1 to 1:3 of polymer:ceramic by weight, and wherein the composition comprises or is a composite of the polymer and the ceramic having improved printability and/or having an improved elastic modulus and/or improved stress at failure (e.g., as compared to a blend of the polymer and the ceramic).

In some embodiments, the composite of polymer and ceramic has an internal microporous structure. In some embodiments, the composite of polymer and ceramic in the form of a 4 mm cube with 0.8 mm pores has an elastic modulus of from 15 to 25 MPa. In some embodiments, the composite of polymer and ceramic has an accelerated degradation as compared to a composite having a higher ratio of biocompatible polymer:biocompatible ceramic. In some embodiments, the composite of polymer and ceramic has increased water uptake as compared to a composite having a higher ratio of biocompatible polymer:biocompatible ceramic.

In some embodiments, the composition is provided as a filament useful for fused deposition modeling (FDM) three-dimensional printing. In some embodiments, the filament is provided on a spool. In some embodiments, the composition is provided as a powder or pellets useful for fused deposition modeling (FDM) three-dimensional printing. In some embodiments, the powder or pellets is provided in a cartridge.

Also provided is a medical implant (e.g., a bone implant) composition comprising a polymer (such as PCL), and a ceramic (such as TCP) as taught herein. In some embodiments, the implant is produced by fused deposition modeling (FDM) 3D printing.

Further provided is a method of making a composition comprising a composite of a polymer (e.g., a biocompatible polymer such as PCL), and a ceramic (e.g., a biocompatible ceramic such as TCP), wherein the polymer and ceramic are present in the composition at a ratio of from 3:1 to 1:3 of biocompatible polymer:biocompatible ceramic by weight, the method comprising one or more of the steps of: providing an organic solvent with the biocompatible polymer dissolved therein, adding the biocompatible ceramic to the organic solvent, wherein the biocompatible ceramic has an average particle size of about 100 nanometers, and wherein the organic solvent is at a temperature of 20-60° C., to form a mixture of the biocompatible polymer and the biocompatible ceramic, sonicating the mixture of the biocompatible polymer and the biocompatible ceramic (e.g., at a frequency of 15 or 20 to 25 or 30 kHz), to form a sonicated mixture, and drying the sonicated mixture to form said composition.

In some embodiments, providing the organic solvent with the polymer dissolved therein comprises one or more of the steps of: mixing the biocompatible polymer with an organic solvent, and heating the organic solvent to its boiling point until the biocompatible polymer dissolves.

In some embodiments, drying the sonicated mixture comprises one or more of the steps of: drying the sonicated mixture in a vacuum oven, cryomilling the sonicated mixture to form a powdered composition, and then drying the powdered composition in a vacuum oven.

Also provided is method of making a medical implant, said method comprising printing a composition as taught herein. In some embodiments, the printing comprises fused deposition modeling, such as fused deposition modeling through a nozzle that is from 50 microns to 300 microns in size.

The foregoing and other objects and aspects of the present invention are explained in further detail in the drawings herein and the specification set forth below. The disclosures of all United States patent references cited herein are incorporated by reference herein in their entirety.

DETAILED DESCRIPTION OF EMBODIMENTS

The present invention is now described more fully hereinafter with reference to the accompanying drawings, in which embodiments of the invention are shown. This invention may, however, be embodied in different forms and should not be construed as limited to the embodiments set forth herein; rather these embodiments are provided so that this disclosure will be thorough and complete and will fully convey the scope of the invention to those skilled in the art.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

As used herein, "biocompatible" means that the substance is not unduly harmful, e.g., not unduly toxic, injurious, physiologically reactive and/or causing immunological rejection, to living tissue when used for treatment as taught herein.

Polymers

Polymers that may be used in accordance with embodiments of the present invention may be any suitable biocompatible polymeric material, including biodegradable or bioerodible polymers, or polymers that are stable or inert in vivo. Examples include, but are not limited to poly(lactic acid) polymers, poly(glycolic acid) polymers, poly(lactide-co-glycolides) (PLGA), poly(urethanes), poly(siloxanes) or silicones, poly(ethylene), polyvinyl pyrrolidone), poly(2-hydroxy ethyl methacrylate), poly(N-vinyl pyrrolidone), poly(methyl methacrylate), polyvinyl alcohol) (PVA), poly (acrylic acid), polyvinyl acetate), polyacrylamide, poly(ethylene-co-vinyl acetate), poly(ethylene glycol), poly(methacrylic acid), polylactic acid (PLA), polyglycolic acids (PGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO), and polyorthoesters or a co-polymer formed from at least two members of the group. In some embodiments, the polymer comprises, consists of or consists essentially of an aliphatic polyester.

In some embodiments, the polymer is poly-L-lactic acid, poly(glycolic acid), polycaprolactone, polystyrene, polyethylene glycol, or a copolymer thereof (such as poly(lactic-co-glycolic acid)). In some embodiments, the polymer is polycaprolactone (PCL).

Ceramics

Examples of suitable ceramic materials that may be used in accordance with embodiments of the present invention include, but are not limited to, tetracalcium phosphate, tricalcium phosphate, calcium alkali phosphate ceramic, calcium phosphorus apatite, bioglass, calcium carbonate, calcium hydroxide, calcium oxide, calcium fluoride, calcium sulfate, magnesium hydroxide, hydroxyapatite, calcium phosphorus apatite, magnesium oxide, magnesium carbonate, magnesium fluoride, silver nanoparticles, carbon-based nanoparticles (e.g., carbon nanotubes), allograft bone, and mixtures thereof. See, e.g., U.S. Pat. Nos. 6,869,445 and 5,281,265.

In some embodiments, the ceramic comprises hydroxyapatite, tricalcium phosphate, or a mixture thereof. In some embodiments, the ceramic is tricalcium phosphate (TCP).

In some embodiments, the ceramic is in the form of nanoparticles. In some embodiments, the ceramic has an average particle size of from 10, 20, 30, 40 or 50 nanometers to 80, 90, 100, 200, 300 or 400 nanometers. In some embodiments, the ceramic has an average particle size of up to 1 micron.

Compositions and Methods of Use

Provided herein are compositions comprising a biocompatible polymer and a biocompatible ceramic. In some embodiments, the biocompatible polymer and biocompatible ceramic are present in the composition at a ratio, by weight, of from 3:1 to 1:3 of biocompatible polymer:biocompatible ceramic. In some embodiments, the biocompatible polymer and biocompatible ceramic are present in the composition at a ratio, by weight, of from 2:1 to 1:2 of biocompatible polymer:biocompatible ceramic. In some embodiments, the biocompatible polymer and biocompatible ceramic are present in the composition at a ratio, by weight, of from 1.5:1 to 1:1.5 of biocompatible polymer:biocompatible ceramic. In some embodiments, the biocompatible polymer and biocompatible ceramic are present in the composition at a ratio, by weight, of 1-25:1 to 1:1.25 of biocompatible polymer:biocompatible ceramic. In some embodiments, the biocompatible polymer and biocompatible ceramic are present in the composition at a ratio, by weight, of 1:1 of biocompatible polymer:biocompatible ceramic.

The composition may be tailored or adjusted to achieve mechanical properties suitable for desired tissue treatment. For example, a ratio of PCL:TCP of approximately 1:1 by weight may be able to achieve a compression modulus similar to trabecular bone.

In some embodiments, the composition is provided as composite of a biocompatible polymer and a biocompatible ceramic (e.g., composite particles thereof). "Composite" as used herein refers to the polymer and ceramic being combined in such a way that the ceramic is substantially incorporated (e.g., intercalated) into the polymer (see FIGS. 5A-5B). In some embodiments, the composite has an improved (i.e., higher) elastic modulus and/or improved (i.e., higher) stress at failure as compared to a blend of said biocompatible polymer and said biocompatible ceramic wherein the ceramic is not substantially incorporated into the polymer (see FIG. 3). For example, a melt-pressed sheet of the composite may have an elastic modulus of from 1200 or 1300 MPa to 1500 or 1600 MPa under tensile loading, and/or a stress at failure of from 5000 or 6000 kPa to 8000, 9000 or 10000 kPa. As another example, a 4 mm cube with 0.8 mm pores may have an elastic modulus of from 15 to 25, 27 or 30 MPa under compressive loading.

In some embodiments, the composite of polymer and ceramic has improved printability (e.g., printing at higher print speeds and/or resolution) as compared to a blend of the polymer and ceramic. For example, in some embodiments the composition has rheological properties such that it is extrudable through a 300, 200, 100, or 50 micron nozzle of, e.g., a fused deposition modeling (FDM) system. By "extrudable" is meant the composition is consistently usable with the nozzle without significant and/or frequent failure such as, e.g., clogging the nozzle.

In some embodiments, the composite of polymer and ceramic has an internal microporous structure. In some embodiments, the micropores are an average of from about 1 or 5 microns to about 30, 50 or 100 microns in diameter.

Compositions of the invention may optionally include additional ingredients such as, e.g., growth factors, antibiotics, etc. "Antibiotic" as used herein includes any suitable antibiotic, including, but not limited to, cefazolin, vancomycin, gentamycin, erythromycin, bacitracin, neomycin, penicillin, polymycin B, tetracycline, biomycin, chloromycetin, streptomycin, ampicillin, azactam, tobramycin, clindamycin, gentamicin and combinations thereof. See, e.g., U.S. Pat. No. 6,696,073. In some embodiments, the antibiotic is a water soluble antibiotic.

Compositions taught herein may be provided in the form of products suitable for use in three-dimensional priming or extrusion devices, such as fused deposition modeling (FDM). In some embodiments, the composition is provided in the form of a filament having a diameter of, for example, from 1 or 2 millimeters to 5, 8 or 10 millimeters, and/or a length of, for example, from 1, 2 or 5 meters to 20, 50 or 100 meters. In some embodiments, the filament is provided on a spool. In some embodiments, the composition is provided as pellets (e.g., having a diameter of from 1 or 2 millimeters to 5, 8 or 10 millimeters). In some embodiments, the composition is provided as a powder. In some embodiments, the pellets or powder is provided in a cartridge.

Extrudable compositions may be used with any suitable deposition apparatus, including, but not limited to, that described in Kang et al., US 2012/0089238.

In some embodiments, the depositing step is a patterned depositing step; that is, deposition is carried out so that the deposited composition is deposited in the form of a regular or irregular pattern, such as a regular or irregular lattice, grid, spiral, etc. See, e.g., Kang et al., US 2012/0089238; Teoh et al., U.S. Pat. No. 8,702,808; and Teoh et al., U.S. Pat. No. 6,730,252.

In some embodiments, the deposition apparatus includes and/or is operatively associated with a computer-aided drafting and/or computer aided manufacturing (CAD/CAM) system to design the products to be created or convert images to a product design, control the dispensers, XYZ axis positioning, and or other functions. Such CAD/CAM systems are known to those skilled in the art and can be implemented in combination with the present invention in accordance with known techniques or variations thereof that will be apparent to those skilled in the art. See, e.g., U.S. Pat. Nos. 7,472,044; 7,413,597; 7,308,386; 6,804,568; 6,775,581; 6,773,713; 6,594,339; 6,379,593; 5,930,152; and 5,757,649: the disclosures of which are incorporated by reference herein in their entirety.

Compositions as taught herein may be provided (e.g., by being printed, melted or molded) in the form of a scaffold useful for bone and/or cartilage regeneration, including composite tissues such as the osteotendinous junction, osteoligamentous, osteochondral interface, etc. Such scaffolds may, accordingly, be used in methods of treatment for bone and/or cartilage injuries such as breaks, tears, fractures, etc., inclusive of injuries due to surgical procedures (e.g., tumor removal) and/or for denial or facial treatment or cosmetic procedures.

"Bone" as used herein includes any bone or bone tissue, such as, for example: the pelvis; long bones such as the tibia, fibia, femur, humerus, radius, and ulna, ribs, sternum, clavicle, skull, mandible, etc. Other craniofacial bones include, but are not limited to, the inferior nasal concha, lacrimal bone, maxilla, nasal hone, palatine bone, vomer, zygomatic bone, alveolar ridge, etc.

"Fracture" or "break" as used herein with respect to bones includes any type thereof, including open or closed, simple or compound, comminuted fractures, and fractures of any location including diaphyseal and metaphyseal. "Fracture" as used herein is also intended to include defects such as holes, gaps, spaces or openings, whether naturally occurring, the result of trauma or surgically induced (e.g., by surgical removal of undesired tissue from bone).

In some embodiments, the scaffold may be seeded with cells during or after the biofabrication. Such cells may include, but are not limited to, mammalian cells (e.g., dog, cat, primate, human), including stem cells (e.g., embryonic, amniotic fluid, etc.), progenitor cells and differentiated cells. Particular examples include, but are not limited to, chondrocytes, tenocytes, odontoblasts, and osteoblasts, as well as progenitors thereof.

Stem cells have the ability to replicate through numerous population doublings (e.g., at least 60-80), in some cases essentially indefinitely, and also have the ability to differentiate into multiple cell types (e.g., is pluripotent or multipotent). It is also possible for cells to be transfected with a compound of interest that results in the cells becoming immortalized (i.e., able to double more than 50 times). For example, it has been reported that mammalian cell transfection with telomerase reverse transcriptase (hTERT) can immortalize neural progenitor cells (See U.S. Pat. No. 7,150,989 to Goldman et al.).

"Embryonic stem cell" as used herein refers to a cell that is derived from the inner cell mass of a blastocyst and that is pluripotent.

"Amniotic fluid stem cell" as used herein refers to a cell, or progeny of a cell, that (a) is found in, or is collected from, mammalian amniotic fluid, mammalian chorionic villus, and/or mammalian placental tissue, or any other suitable tissue or fluid from a mammalian donor, (b) is pluripotent; (c) has substantial proliferative potential, (d) optionally, but preferably, does not require feeder cell layers to grow in vitro, and/or (c) optionally, but preferably, specifically binds c-kit antibodies (particularly at the time of collection, as the ability of the cells to bind c-kit antibodies may be lost over time as the cells are grown in vitro).

"Pluripotent" as used herein refers to a cell that has complete differentiation versatility, e.g. the capacity to grow into any of the animal's cell types. A pluripotent cell can be self-renewing, and can remain dormant or quiescent with a tissue. Unlike a totipotent cell (e.g., a fertilized, diploid egg cell) a pluripotent cell cannot usually form a new blastocyst.

"Multipotent" as used herein refers to a cell that has the capacity to grow into any of a subset of the corresponding animal cell types. Unlike a pluripotent cell, a multipotent cell does not have the capacity to form all of the cell types of the corresponding animal.

"Cartilage cells" include those cells normally found in cartilage, which cells include chondrocytes. "Chondrocytes" produce and maintain the extracellular matrix of cartilage, by, e.g., producing collagen and proteoglycans. Cartilage is a highly specialized connective tissue found throughout the body, and its primary function is to provide structural support for surrounding tissues (e.g., in the ear and nose) or to cushion (e.g., in the trachea and articular joints). Types of cartilage include hyaline cartilage (articular joints, nose, trachea, intervertebral disks (NP), vertebral end plates), elastic cartilage (tendon insertion site, ligament insertion site, meniscus, intervertebral disks (AP)), costochondral cartilage (rib, growth plate), and fibrocartilage (ear). The loss of cartilage in a subject can be problematic, as it has a very limited repair capacity.

"Mesenchymal stem cells" or "MSCs" are progenitors of chondrocytes. MSCs can also differentiate into osteoblasts. Cartilage cells/tissues used with the compositions described herein are useful for, among other things, implantation into a subject to treat cartilage injury or disease.

"Bone cells" include those cells normally found in bone, and include osteoblasts, osteoclasts, osteocytes, and any combination thereof. Bone cells/tissues used with the compositions described herein are useful for, among other things, implantation into a subject to treat bone fractures or defects, and/or promote bone healing.

Cells may be syngeneic (i.e., genetically identical or closely related, so as to minimize tissue transplant rejection), allogeneic (i.e., from a non-genetically identical member of the same species) or xenogeneic (i.e., from a member of a different species). Syngeneic cells include those that are autogeneic (i.e., from the subject to be treated) and isogeneic (i.e., a genetically identical but different subject, e.g., from an identical twin). Cells may be obtained from, e.g., a donor (either living or cadaveric) or derived from an established cell strain or cell line. For example, cells may be harvested from a donor (e.g., a potential recipient of a medical implant composition) using standard biopsy techniques known in the art.

In some embodiments, one or more active or therapeutic agents can be included in the composition or scaffold made therefrom. The same or different agents can be included in different regions. Any suitable active agent (e.g., in an amount to facilitate the growth and/or differentiation of cells) can be used. Examples include, but are not limited to, transforming growth factor-alpha (TGF-alpha), transforming growth factor-beta (TGF-beta), platelet-derived growth factor (PDGF), fibroblast growth factor (FGF), nerve growth factor (NGF), brain derived neurotrophic factor, cartilage derived factor, bone growth factor (BGF), basic fibroblast growth factor, insulin-like growth factor (IGF), vascular endothelial growth factor (VEGF), granulocyte colony stimulating factor (G-CSF), hepatocyte growth factor, glial neurotrophic growth factor (GDNF), stem cell factor (SCF), keratinocyte growth factor (KGF), and skeletal growth factor. Stromal-derived factor (SDF), peptides such as substance P (SP), agrin, small molecules such as adenosine, etc. See. e.g., U.S. Pat. No. 7,531,503.

"Subjects" who may be treated with scaffolds made in accordance with the present invention are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult and geriatric subjects.

Subjects may also include animal subjects, particularly vertebrate subjects, e.g., mammalian subject such as canines, felines, bovines, caprines, equines, ovines, porcines, rodents (e.g., rats and mice), lagomorphs, non-human primates, etc., or fish or avian subjects, for, e.g., veterinary medicine and/or research or laboratory purposes. "Treat" refers to any type of treatment that imparts a benefit to a subject, e.g., a patient afflicted with a trauma or a disease resulting in loss or damage to bone and/or cartilage, including dental or other tissue reconstruction. For example, arthritis is a disease that affects cartilage. Treating includes actions taken and actions refrained from being taken for the purpose of improving the condition of the patient (e.g., the relief of one or more symptoms), delay in the onset or progression of the disease, etc. In some embodiments, treating includes reconstructing bone and/or cartilage tissue (e.g., where such tissue has been damaged or lost by injury or disease) by implanting a scaffold into a subject in need thereof. Scaffolds may be implanted, e.g., at or adjacent to the site of injury, and/or at another site in the body of a subject that would impart a benefit to the subject, as would be appreciated by one of skill in the art. Scaffolds or implants may also be used in treatment for cosmetic or plastic surgery purposes.

In some embodiments, scaffolds as taught herein may be resorbable in vivo over a time of from 1 month to 6 months, e.g., from 1, 2, 3, 4 or 5 to 6 months, from 1, 2, 3 or 4 to 5 or 6 months, from 1, 2 or 3 to 4, 5 or 6 months, or from 1 or 2 to 3, 4, 5 or 6 months.

In some embodiments, the fabricated constructs are composed of two parts: 1) a cell-containing gel or hydrogel structure and 2) a solidified polymer or polymer-based composite or structural polymer scaffold, as taught herein. The polymer scaffold provides such a frame to protect the cell-contained gel structure from external loads or disruption. See Kang et al., US Patent Application Pub. No. US 2012/0089238, which is incorporated by reference herein in its entirety.

Methods of Making Extrudable Compositions

Provided herein are methods of making a composition comprising a biocompatible polymer and a biocompatible ceramic, wherein said composition is extrudable. In some embodiments, the method includes one or more of: providing an organic solvent with the biocompatible polymer dissolved therein, adding the biocompatible ceramic, wherein the organic solvent is at a temperature of, for example, 20 to 60 degrees Celsius (depending on the strength of the solvent, melting point of the polymer and boiling point of the solvent) to form a mixture of the biocompatible polymer and the biocompatible ceramic, sonicating the mixture of the biocompatible polymer and the biocompatible ceramic at a frequency of, for example, 10, 15 or 20 to 25, 30 or 40 kilohertz (kHz), to form a sonicated mixture, and drying the sonicated mixture to form the composition.

In some embodiments, providing the organic solvent with the biocompatible polymer dissolved therein may include one or more of the steps of: mixing the biocompatible polymer with an organic solvent, heating the organic solvent to its boiling point (e.g., refluxing) until the biocompatible polymer dissolves, to thereby provide the organic solvent with the biocompatible polymer dissolved therein.

In some embodiments, drying the sonicated mixture may comprise one or more of the steps of: drying the sonicated mixture in a vacuum oven, cryomilling the sonicated mixture to form a powdered composition, and then drying the powdered composition in a vacuum oven, to thereby dry the sonicated mixture.

The present invention is explained in greater detail in the following non-limiting examples.

EXAMPLES

Example Method of Making PCL-TCP Composite Via Solvent/Milling Method (SM)

In a glass beaker with a stir bar, mix PCL with organic solvent (e.g., chloroform or acetone) (e.g., 10 grams of PCL and 100 mL solvent)
While stirring, cover and heat to boiling point and leave at a simmering level until PCL dissolves completely (stir bar can be set to about 60-100 rpm)
Continue stirring while adding TCP powder (e.g., nano powder—100 nm average particle size)
Allow to mix thoroughly with stir bar
Remove from heat/stirring and insert sonicator horn
Sonicate for about 1-3 minutes
Return to stirring with stir bar
Leave partially covered until stir bar no longer overcomes viscosity
Place container in vacuum oven overnight (used 45° C. and −12 psi)
Cryomill material (5-3 min cycles at 10c/s)
Dry thoroughly in vacuum oven overnight
Powder is ready for 3D printing or filament fabrication Example Comparison of PCL/TCP Materials TEM and tensile data indicate material difference based on PCL/TCP blend method. Both materials are 1:1 PCL/TCP (wt. %).

TEM of Material Powder in Ethanol Suspension

Figure 1:
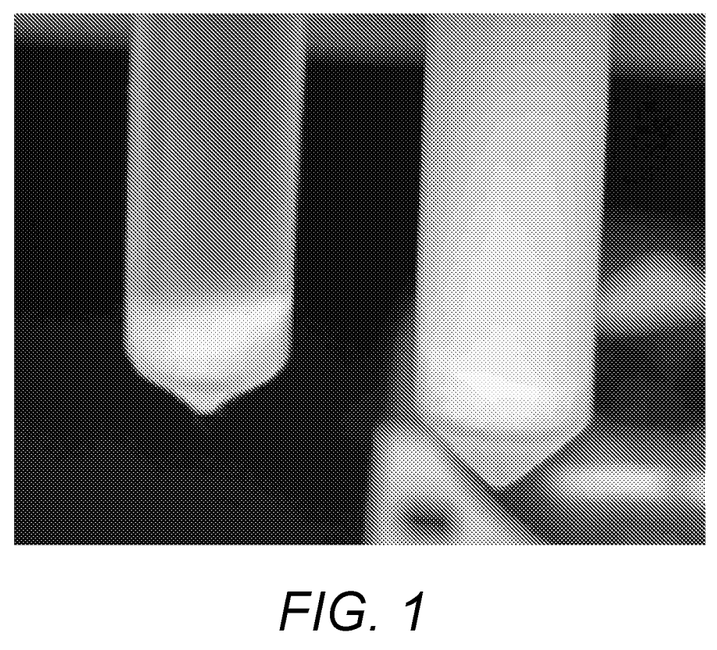
FIG. 1 is a photograph demonstrating how the solvent/milling method as taught herein results in larger PCL particles. On the left is shown particles resulting from the Solvent/Milling method (SM), and on the Right is particles from the Cryo-milling (CM) alone. The TCP particles suspend, while the larger PCL particles sink.
Figure 2:
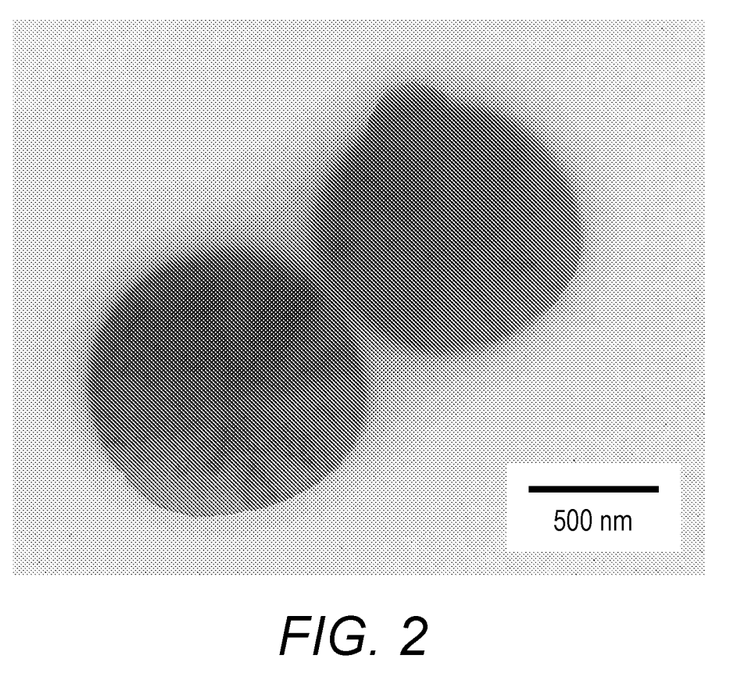
FIG. 2 is a magnified image of composite PCL/TCP particles generated by process including solvent blending step.
Figure 3:
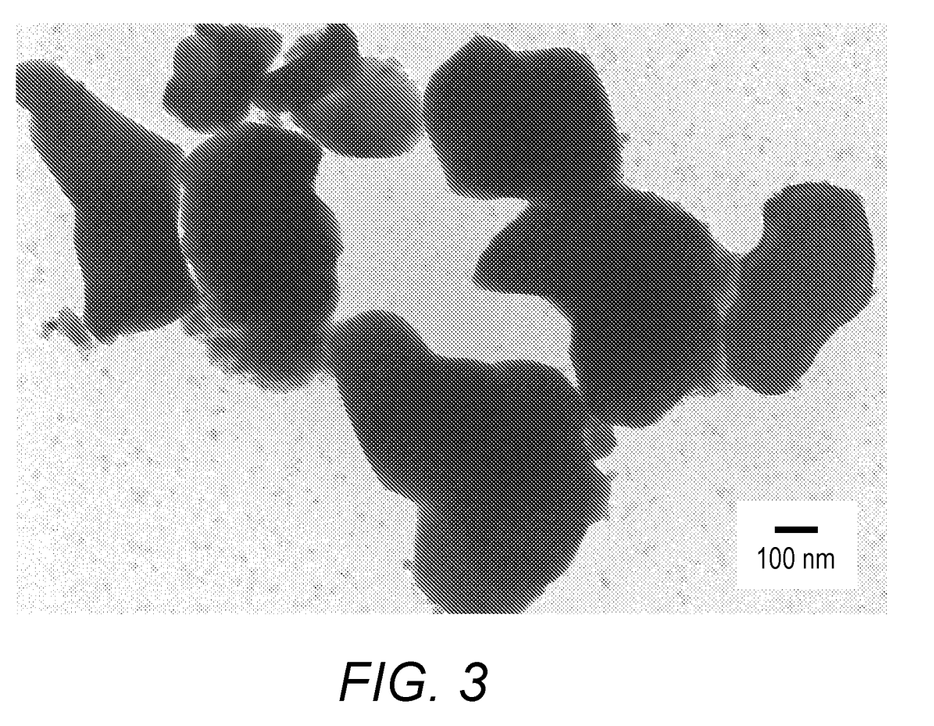
FIG. 3 is a magnified image of particles of TCP aggregating without evidence of incorporated PCL after the cryo-mill blending.

As shown in FIGS. 1-3, the Solvent/Milling method (SM) results in a powder with composite particles, whereas Cryomilling (CM) alone (physical blend of PCL and TCP that is simply cryomilled together) appears to produce a powder with two distinct phases. Ethanol suspensions were distinct. CM suspension produced mainly TCP aggregates, while SM did not suspend well and particles appear to be composite in nature.

Tensile Test of Melt-Pressed Sheet

Figure 4:
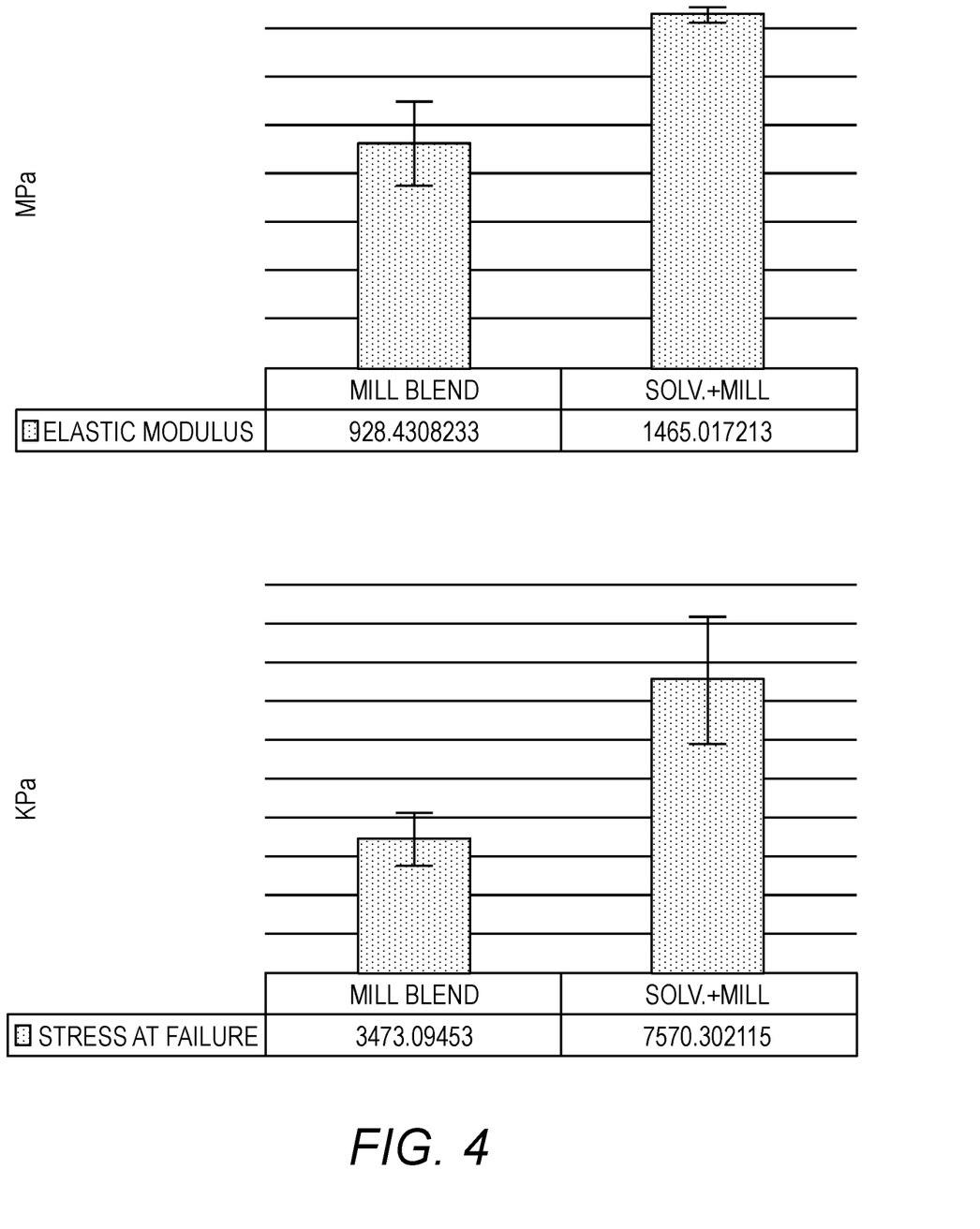
FIG. 4 shows improved elastic modulus and stress at failure of the SM particles as compared to the CM.

Melt-pressed sheets were cut into dog bone test specimens and destructively tested in tensile loading. Sheets were produced by pressing 2 g of powder between heated platens in a hydraulic press. Platens were heated to 120° C. and powder was allowed to preheat for 5 minutes prior to application of pressure up to 2 metric tons then removed and cooled to room temperature. Sheets measured 150-200 m in thickness. A dog bone shaped punch was used to stamp out tensile specimen from the sheets. This fabrication method represents melt-extrusion printing or laser sintering fabrication. The resulting data shown in FIG. 4 indicates better performance from the SM material by means of higher Elastic Modulus and higher Stress at Failure.

Example Use of PCL-TCP Composition for Bioprinted Calvarial Bone Reconstruction

Bioprinted constructs for calvarial bone reconstruction were formed of PCL doped with tricalcium phosphate (TCP) nanoparticles (Berkeley Advanced Biomaterials, Berkeley, Calif.) at a 1:1 ratio by weight, with cell-laden hydrogel dispensed in an interleaved crosshatch pattern. The mixture of PCL and TCP was printed through a 200-μm diameter nozzle (TECDIA Inc., Campbell, Calif.) with 780 kPa compressed air. These materials were heated to 112° C. in the heating chamber of the Integrated Tissue/Organ Printing system (ITOP) to produce a beam width of 200 μm. The printed PCL/TCP architecture provided an internal porosity of approximately 70%. The top and bottom surfaces of the construct were primed with beam heights of 50 μm and 220 μm pitch resulting in 100 μm thick region of low porosity to minimize host cell infiltration.

Cell-laden hydrogel was printed within the internal pores of the PCL/TCP structure, which was produced with 115 μm beam height and 670 μm pitch with repealing layers such that resultant wall heights reached 345 μm. The cell-laden hydrogel was composed of $5 \times 10^6$ human amniotic fluid stem cells (hAFSCs) per ml of the hydrogel and printed through a 300 µm diameter Teflon-lined needle nozzle (Musashi Engineering Inc.) at 60 kPa. After printing, constructs were treated with a thrombin solution to induce fibrinogen conversion to fibrin, as well as osteogenic culture conditions. Constructs were incubated in osteogenic differentiation media for 10 days before implantation.

Results

To study maturation of bioprinted bone in vivo, rat calvarial bone constructs were fabricated in a circular shape (8 mm diameter×1.2 mm thickness) with hAFSCs cultured in osteogenic media for 10 days, and then implanted in a calvarial bone defect region of Sprague Dawley rats (n=4). Constructs were analyzed 5 months after implantation. The bioprinted constructs showed newly-formed vascularized bone tissue throughout the implants, including the central portion, with no necrosis, whereas the untreated defect and scaffold-only treated control groups showed fibrotic tissue ingrowth and minimal bone tissue formation restricted to the periphery of the implant, respectively. The modified Tetrachrome staining confirmed mature bone and osteoid formation. Von Willebrand factor (vWF) immunostaining showed large blood vessel formation within newly formed bone tissue throughout the bioprinted bone constructs, including the central portion, whereas the nontreated and scaffold-only groups had only limited vascularization restricted to the periphery of the implant.

See also Kang et al., "A 3D bioprinting system to produce human-scale tissue constructs with structural integrity," Nature Biotechnology 34:312-319 (2016).

3D Printed Structures of PCL with Variations of TCP Loading

Figure 5A:
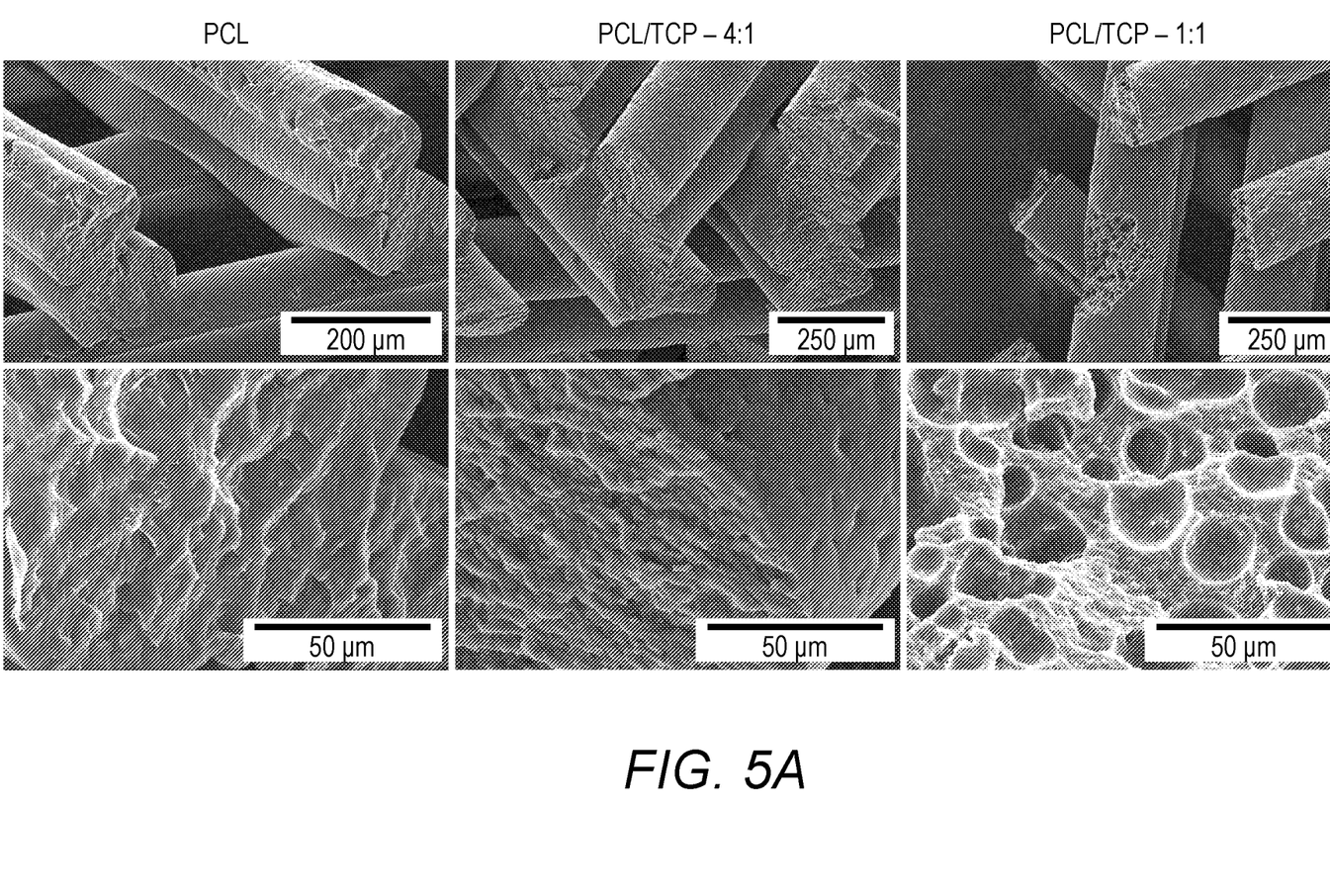
FIG. 5A is an image showing the TCP Loading Effect on PCL composite structure of the material.
Figure 5B:
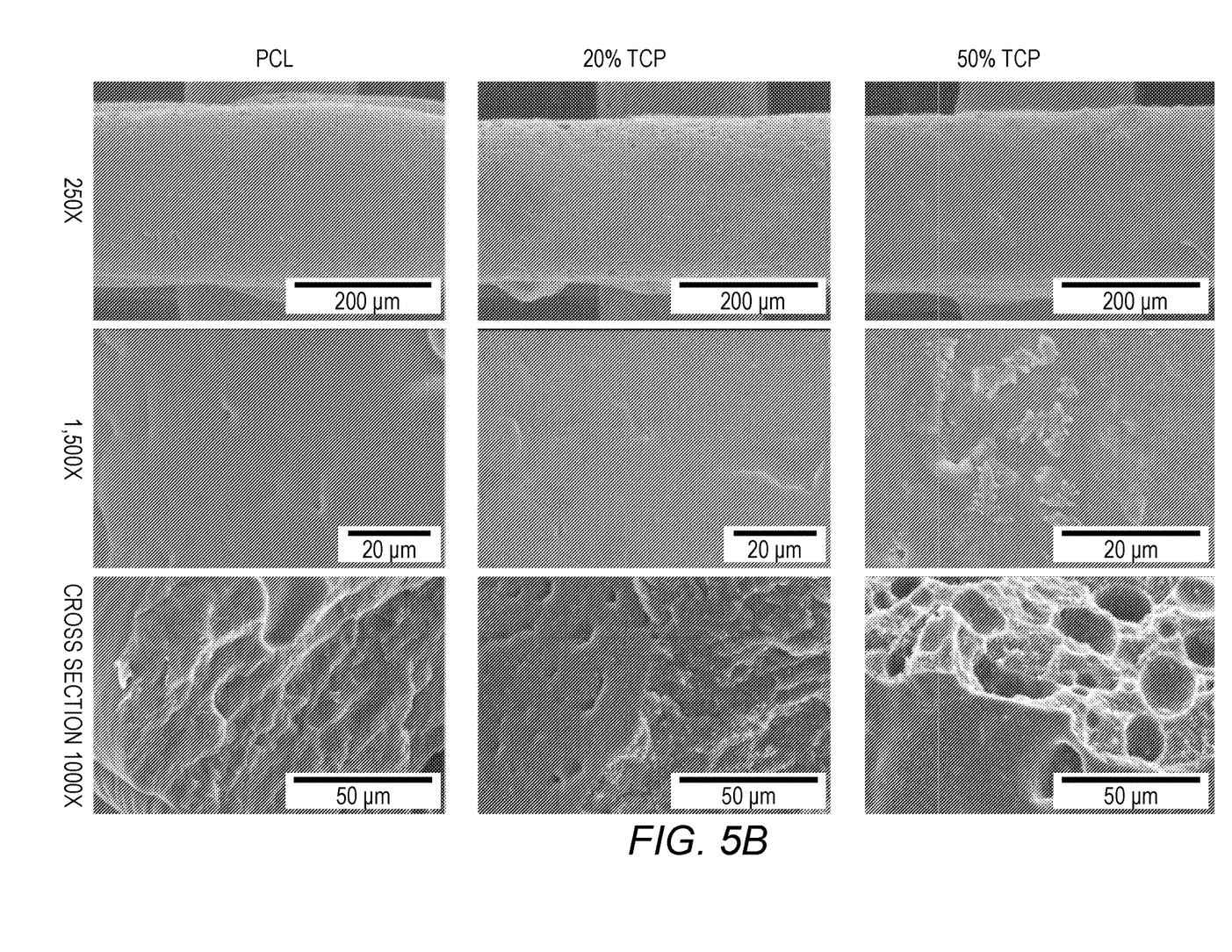
FIG. 5B is another image showing the TCP Loading Effect on PCL. Scanning electron micrographs of printed structures of 100% PCL, PCL/TCP (20% TCP), PCL/TCP (50% TCP). Surface morphology changed with increasing TCP content, including evidence of calcium phosphate exposure on the surface. Structures were immersed in liquid nitrogen and fractured to visualize the cross section of printed filaments. Increased TCP particles were visualized as well as a morphologic change of the inner structure.
Figure 6:
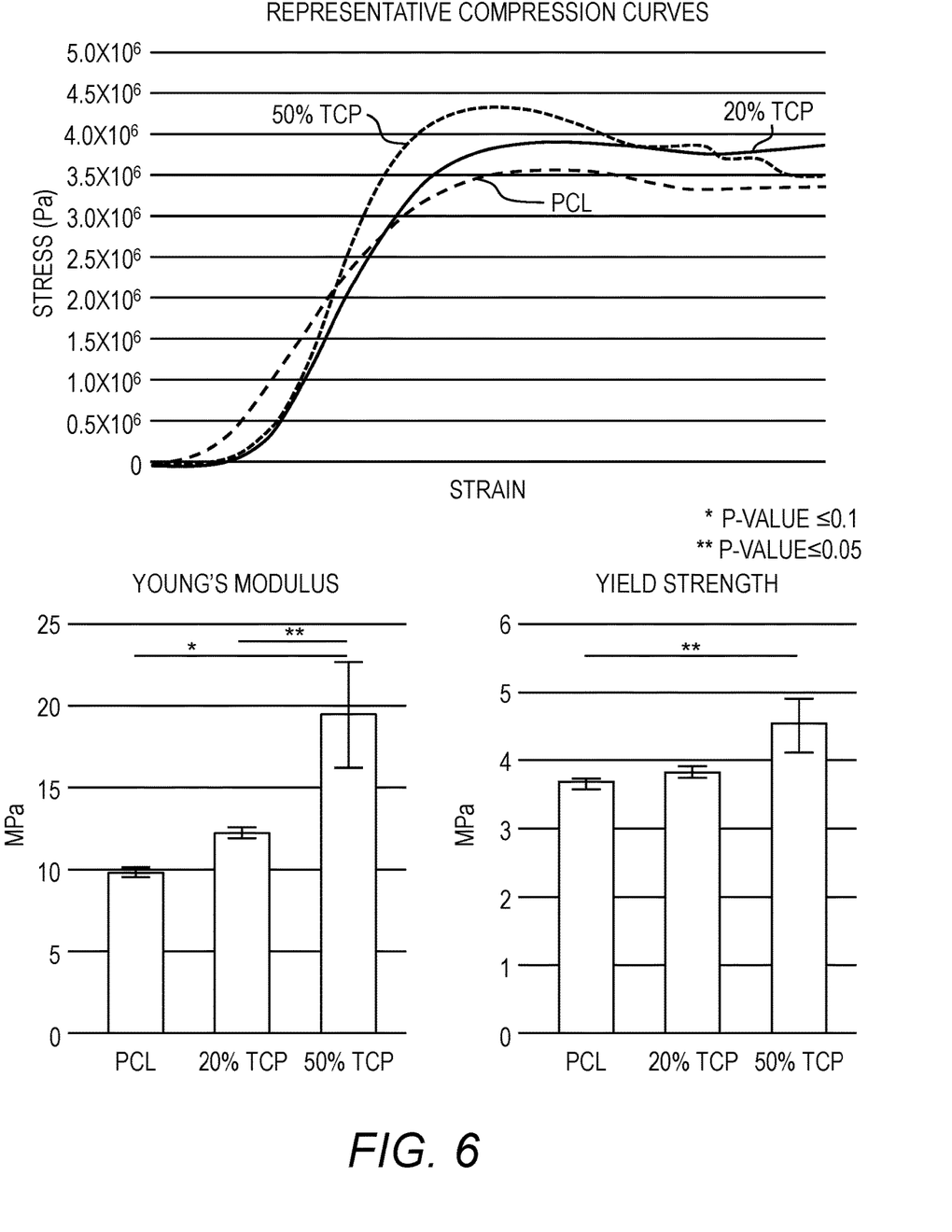
FIG. 6 presents the results of compression, Young's modulus and yield strength on test structures of the materials that were 3D printed as 4 mm cubes. Compression tests were performed on an Instron universal testing system at 1 mm/mm to 25% compression.
Figure 7A:
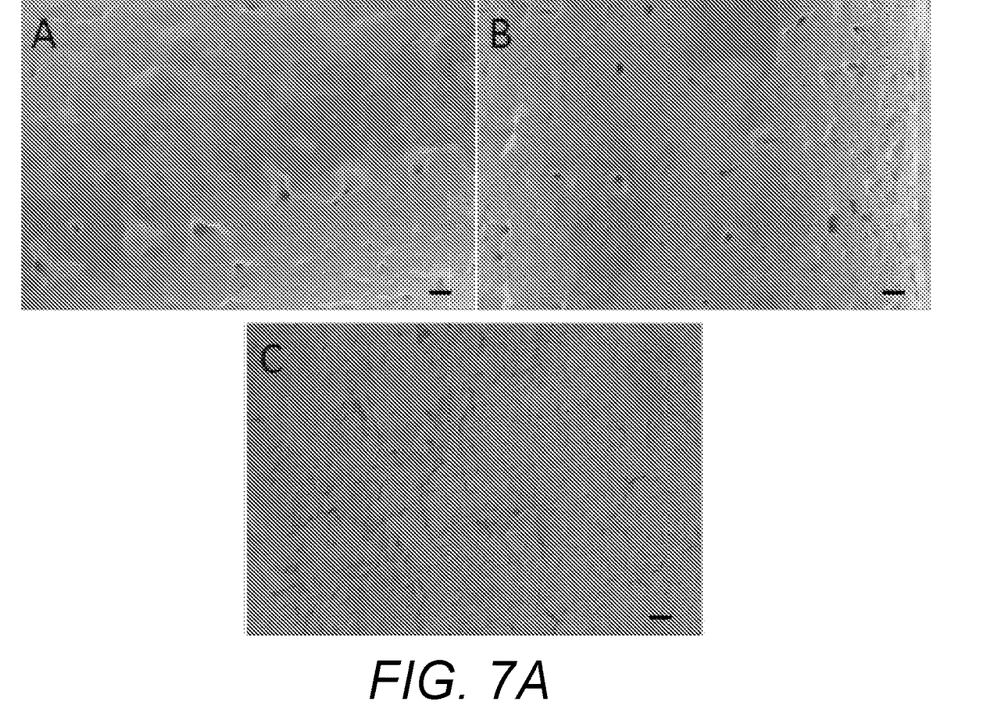
FIG. 7A: Accelerated degradation—SEM: SEM micrographs show surface changes after 24 hrs in 1 N NaOH for accelerated degradation. Panel A: PCL; Panel B: PCL/TCP (20% TCP); Panel C: PCL/TCP (50% TCP). Scale bar—10 µm.
Figure 7B:
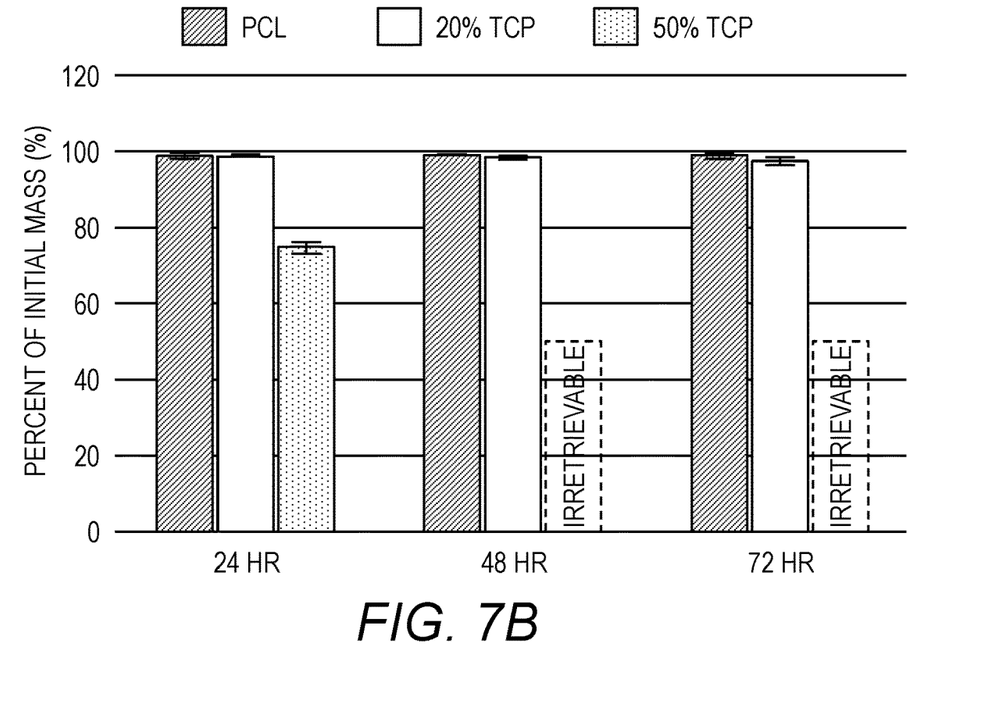
FIG. 7B: Accelerated degradation—Mass: measurements of mass confirm accelerated degradation of the 50% TCP test structures.
Figure 7C:
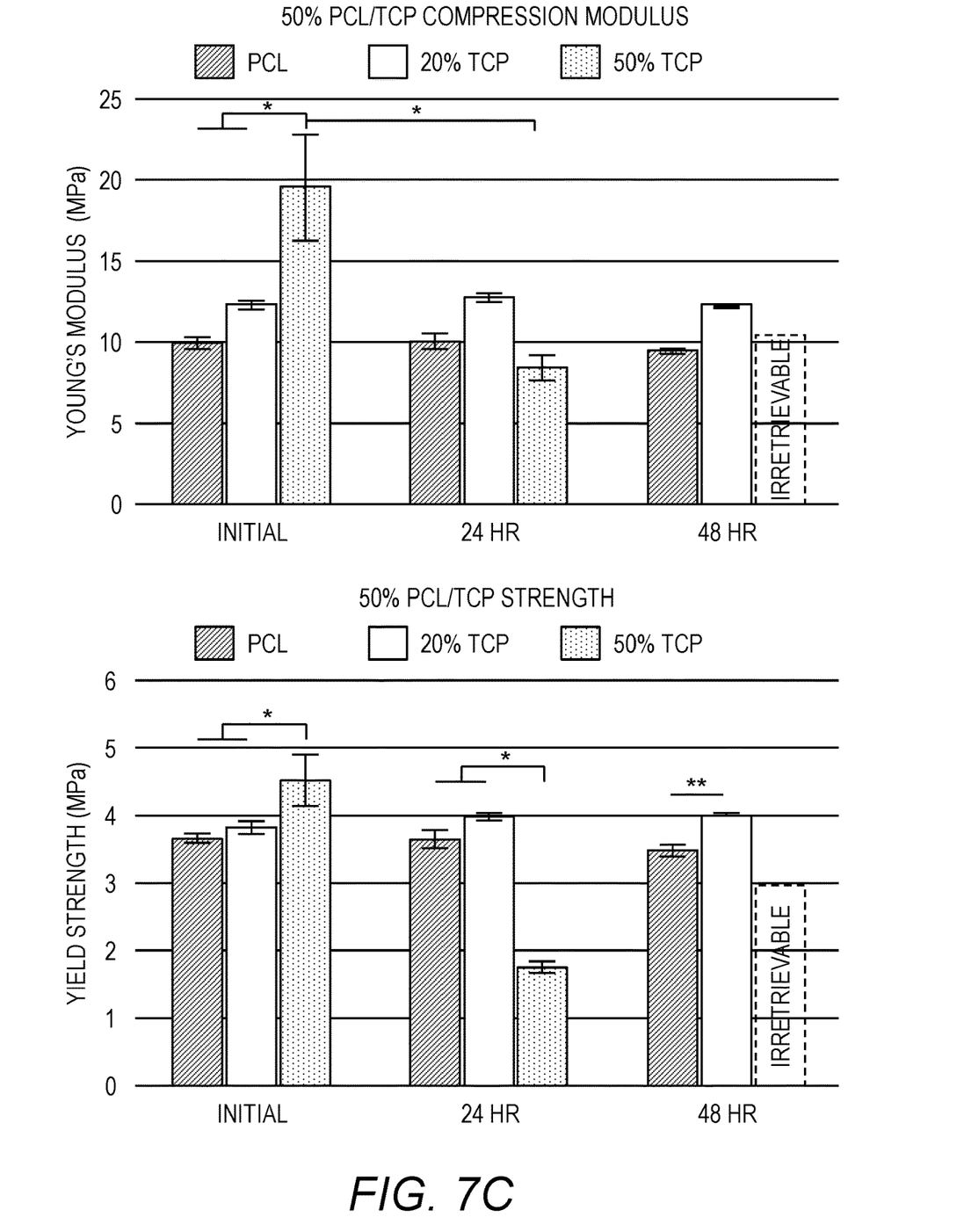
FIG. 7C: Accelerated degradation—Mechanical: Mechanical properties of 4 mm cube structures were evaluated after accelerated degradation for 24, 48 and 72 hrs in 1N NaOH. By 48 hours, the 50% TCP structure collapsed under its own weight, while the PCL and 20% TCP structures maintained their respective properties.
Figure 8:
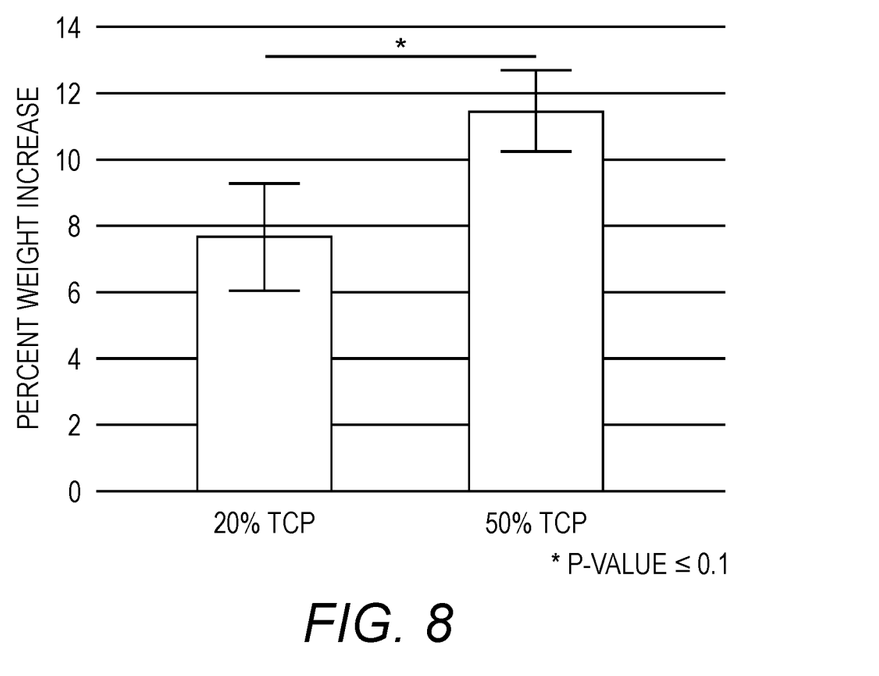
FIG. 8: Water Uptake: Printed PCL structures of 20% and 50% TCP were submerged in water to assess hydrophilic water uptake 50% TCP demonstrated higher water uptake on average.

Shown in FIG. 5 are images of 3D printed structures of polycaprolactone with increasing loading of tricalcium phosphate (TCP) nanoparticles. TCP was incorporated, as described above, by mixing into a solution of polycaprolactone dissolved in an organic solvent. The solvent was then evaporated and the composite milled into a powder. The powder was loaded into a steel cartridge, heated to 120° C., and printed via pneumatic pressure (1.5 MPa). Structures were collected after printing, submerged in liquid nitrogen, and subjected to brittle fracture to observe the cross-section of the printed filaments.

The increase from neat PCL, to 20% TCP (wt %) appears similar in surface and cross-sectional morphology. TCP particles can be observed near the surface at the 20% level. The high TCP content of 50% alters the microstructure of the material comprising the filaments as seen in the images. With no other alterations, the material exhibits an internal microporous structure. Increased numbers of TCP particles are seen at the filament surface and throughout the cross-section.

The foregoing is illustrative of the present invention, and is not to be construed as limiting thereof. The invention is defined by the following claims, with equivalents of the claims to be included therein.

That which is claimed is:

1. A method of making a composition, said composition comprising:
   a biocompatible polymer; and
   a biocompatible ceramic,
   wherein said biocompatible polymer and said biocompatible ceramic are present in said composition at a ratio of from 3:1 to 1:3 of biocompatible polymer:biocompatible ceramic by weight,
   said method comprising:
   providing an organic solvent with the biocompatible polymer dissolved therein,
   adding the biocompatible ceramic to the organic solvent, wherein the biocompatible ceramic has an average particle size of about 100 nanometers, and wherein the organic solvent is at a temperature of 20-60° C., to form a mixture of the biocompatible polymer and the biocompatible ceramic,
   sonicating the mixture of the biocompatible polymer and the biocompatible ceramic at a frequency of 15-30 kHz, to form a sonicated mixture, and
   drying the sonicated mixture to form said composition.

2. The method of claim 1, wherein said providing the organic solvent with the biocompatible polymer dissolved therein comprises the steps of:
   mixing the biocompatible polymer with the organic solvent, and
   heating the organic solvent to its boiling point until the biocompatible polymer dissolves,
   to thereby provide the organic solvent with the biocompatible polymer dissolved therein.

3. The method of claim 1, wherein said drying the sonicated mixture comprises the steps of:
   drying the sonicated mixture in a vacuum oven,
   cryomilling the sonicated mixture to form a powdered composition, and then
   drying the powdered composition in a vacuum oven,
   to thereby dry the sonicated mixture.

4. The method of claim 1, wherein said biocompatible ceramic is tricalcium phosphate (TCP).

5. The method of claim 1, wherein said biocompatible polymer is polycaprolactone (PCL).

6. The method of claim 1, wherein said biocompatible polymer and said biocompatible ceramic are present in said composition at a ratio of from 2:1 to 1:2 of biocompatible polymer:biocompatible ceramic by weight.

7. The method of claim 1, wherein said biocompatible polymer and said biocompatible ceramic are present in said composition at a ratio of from 1.5:1 to 1:1.5 of biocompatible polymer:biocompatible ceramic by weight.

8. The method of claim 1, wherein said biocompatible polymer and said biocompatible ceramic are present in said composition at a ratio of from 1.25:1 to 1:1.25 of biocompatible polymer:biocompatible ceramic by weight.

9. The method of claim 1, wherein said biocompatible ceramic is tricalcium phosphate (TCP) and said biocompatible polymer is polycaprolactone (PCL).

10. The method of claim 1, wherein said biocompatible ceramic is tricalcium phosphate (TCP), said biocompatible polymer is polycaprolactone (PCL), and wherein said biocompatible polymer and said biocompatible ceramic are present in said composition at a ratio of from 1.25:1 to 1:1.25 of biocompatible polymer:biocompatible ceramic by weight.

* * * * *

UNITED STATES PATENT AND TRADEMARK OFFICE
CERTIFICATE OF CORRECTION

PATENT NO. : 11,046,823 B2
APPLICATION NO. : 16/322219
DATED : June 29, 2021
INVENTOR(S) : Carlos Kengla Page 1 of 1

It is certified that error appears in the above-identified patent and that said Letters Patent is hereby corrected as shown below:

In the Specification

Column 5, Line 25: Please correct "1-25:1" to read -- 1.25:1 --

Column 7, Line 35: Please correct "and/or (c)" to read -- and/or (e) --

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*